United States Patent [19]

Schmidt et al.

[11] 4,322,975
[45] Apr. 6, 1982

[54] ULTRASONIC SCANNER

[75] Inventors: Robert A. Schmidt, Torrance; Ewell E. Stevens, Northridge, both of Calif.

[73] Assignee: Northrop Corporation, Hawthorne, Calif.

[21] Appl. No.: 126,304

[22] Filed: Feb. 2, 1980

[51] Int. Cl.³ ............................................. G01N 29/04
[52] U.S. Cl. ....................................................... 73/633
[58] Field of Search ................ 73/633, 634, 635, 639, 73/618, 620, 625, 629; 33/27 C

[56] References Cited

U.S. PATENT DOCUMENTS

| | | | |
|---|---|---|---|
| 3,044,291 | 7/1962 | Klatchko | 73/633 |
| 3,197,871 | 8/1965 | Stein et al. | 33/27 C |
| 3,205,702 | 9/1965 | Joy | 73/639 |
| 3,534,591 | 10/1970 | Phelan | 73/634 |
| 3,938,371 | 2/1976 | Dini | 73/633 |
| 4,103,677 | 8/1978 | Lansiart et al. | 73/625 |

OTHER PUBLICATIONS

Roto-Scanner advertisement NSN6635-00-596-9311.

*Primary Examiner*—Stephen A. Kreitman
*Attorney, Agent, or Firm*—John E. Peele, Jr.; Robert J. Stern; James E. Crawford

[57] ABSTRACT

Apparatus for early detection of fatigue cracks in aircraft structure surrounding fasteners and the like.

An ultrasonic scanner manipulating apparatus is provided with various types of replaceable tips which are used to establish the center of a given fastener, adjustable support legs which provide stability and maintain a proper distance for an ultrasonic transmitting/receiving head assembly to be rotated 360° about the centerline of the fastener, and a liquid filled boot attached to the transmitting/receiving head assembly to assure a reliable signal path between the head and the structure being evaluated.

9 Claims, 5 Drawing Figures

ULTRASONIC SCANNER

STATEMENT OF GOVERNMENT INTEREST

The U.S. Government has rights in this invention pursuant to Contract Number F41608-77-D-A026 awarded by the U.S. Air Force.

BACKGROUND OF THE INVENTION

1. Field of the Invention

The present invention relates generally to ultrasonic inspection devices, and more particularly to an apparatus which detects the presence of fatigue cracks in structure surrounding a rivet or other type of a fastener, as in aircraft structure, for example.

Aircraft maintenance requires constant inspections for cracks resulting from stresses imposed during flight. Failure to detect such cracks in a critical aircraft part or structure can ultimately result in catastrophic failure of the part and, as well known, loss of the aircraft and the lives of the passengers.

2. Description of the Prior Art

Nondestructive testing apparatus using ultrasonic test probe assemblies have been used for inspecting weld beads, bonding adhesives, journals of railroad cars and for sensing the depth of cellular pits or cells in a surface. The present invention is a hand-held device incorporating several unique features, not taught in the prior art, which permits the detection of cracks in a structure around a fastener even when the cracks in the structure are plated or painted over.

PRIOR ART STATEMENT

The following patents are cited as the most pertinent prior art of which the Applicant is aware.

| U.S. PAT. NO. | INVENTORS NAME | DATE |
| --- | --- | --- |
| 3,938,371 | M. Dini | February 17, 1976 |
| 3,534,591 | C. S. Phelan | October 20, 1970 |
| 3,044,291 | G. A. Klatchko | July 17, 1962 |

U.S. Pat. No. 3,938,371 relates to apparatus for measuring the depth of a cell in an object by measuring the reflected ultrasonic beams parallel to the incident of the generated ultrasonic beams. U.S. Pat. No. 3,534,591 relates to an apparatus used to test the bonds between the layers of a bonded structure by measuring changes in the impedance of the structure with an ultrasonically energized piezoelectric crystal. U.S. Pat. No. 3,044,291 relates to an ultrasonic probe which is inserted in a journal box of a railroad car to inspect journals.

While it is possible that more pertinent art exists, Applicant's search is believed to have been conducted with conscientious effort to locate and evaluate the closest prior art available at the time, but the statement is not to be construed as a representation that no better art exists.

SUMMARY OF THE INVENTION

The present invention relates to ultrasonic scanners, and more particularly to a hand-held nondestructive inspection apparatus which provides a means to rotate an ultrasonic transmitting/receiving transducer assembly around a given point such as a fastener or fastener hole in aircraft structures, for example, at a predetermined distance, offset position, and at any particular angle and height relative to the given point. A liquid filled boot is removably attached to the transducer head assembly to assure a reliable signal path between the transmitting/receiving transducer and the structure being inspected.

A primary object of the present invention is to provide hand-held ultrasonic scanner apparatus for detecting fatigue cracks in structural parts, which can detect minute cracks that are not discernable by other inspection methods.

Another object is to provide scanner apparatus which is relatively simple and compact in construction, easy to manipulate, and highly accurate.

Another object is to provide scanner apparatus including a spring loaded contact spindle which accurately establishes the centerline of a fastener around which the transmitting/receiving transducer is rotated.

Another object is to provide an ultrasonic scanner in which the contact spindle is adjustable in height and spring loaded to maintain firm contact with the structure under evaluation.

Another object is to provide a scanner apparatus which includes adjustable support legs to assure stability and maintain height adjustment for a transmitting/receiving transducer to be rotated 360° about the centerline of a fastener or the like.

Another object is to provide a scanner in which a liquid filled boot is employed to assure a reliable signal path between a transmitting/receiving transducer and a structure being inspected.

Another object is to provide an ultrasonic scanner in which the supporting apparatus is provided with one angular and two linear axis vernier adjustments relative to the longitudinal centerline of a contact spindle centering means.

Still, another object is to provide an ultrasonic scanner which includes vernier scale means that provide a direct readout of relative movement between the scanners transmitting/receiving head and the longitudinal centerline of the scanners centering means.

These and other objects and advantages of the present invention, will become clearly apparent from the following detailed description and drawing, all of which is intended to be illustrative of, rather than in any way limiting, the scope of the invention.

DESCRIPTION OF THE PREFERRED EMBODIMENTS

Figure 1:
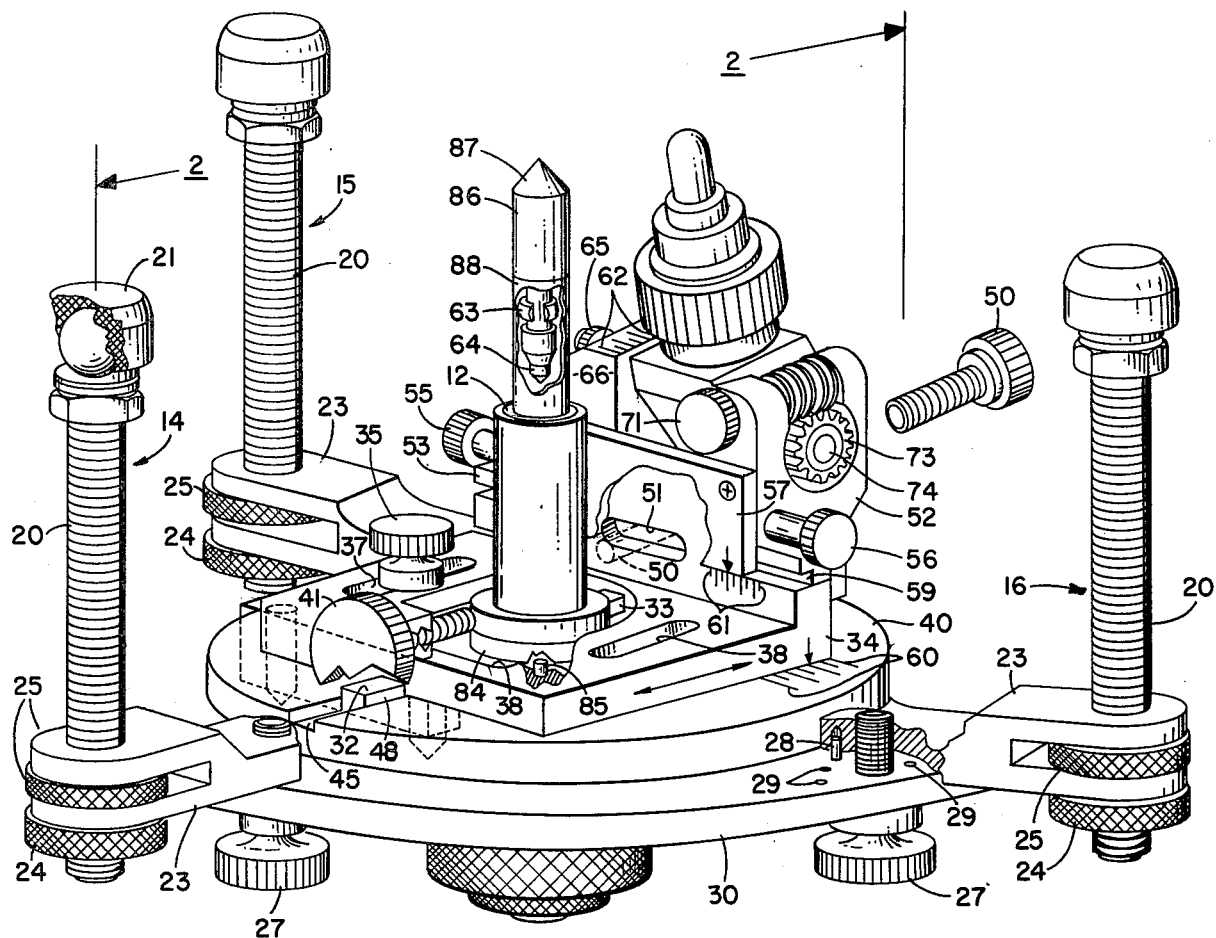
FIG. 1 is a perspective view, partly in cross-section, of the ultrasonic scanner disclosed herein.

Referring to FIG. 1, the ultrasonic scanner 10 is a preferred embodiment of the present invention, and includes a transmitting/receiving head assembly 11 which is adjustable in two linear and one angular axis as well as capable of 360° rotation about a centerline taken along the longitudinal axis of a contact spindle 12.

The transmitting/receiving head assembly 11 includes a liquid filled resilient boot 13. The amount of contact pressure between the structure under inspection (not shown) and the liquid filled resilient boot 13 is controlled by adjustment of three adjustable leg assemblies 14, 15 and 16 respectively, of identical construction.

Each leg assembly includes a threaded leg rod 20. One end of each threaded leg rod 20 is provided with a ball-jointed nylon swivel pad 21 mounted thereon which compensates for any variation in the surface of a structure under evaluation, and assures that the surface of the structure will not be marred by use of the present invention. The other end of the threaded leg rod 20 is adjustably held in one end of a clevis 23 which is, in turn, adjustably held to a base plate 30 by a leg locking screw 27.

The method employed to adjust the length of each leg 20 is to loosen a threaded lock ring 24. The length of the threaded leg rod 20 then being adjusted by rotating a threaded leg adjustment ring 25. After the threaded leg rod 20 has been adjusted, the lock ring 24 retightened to prevent accidental movement of the leg adjustment ring 25.

Figures 2, 5:
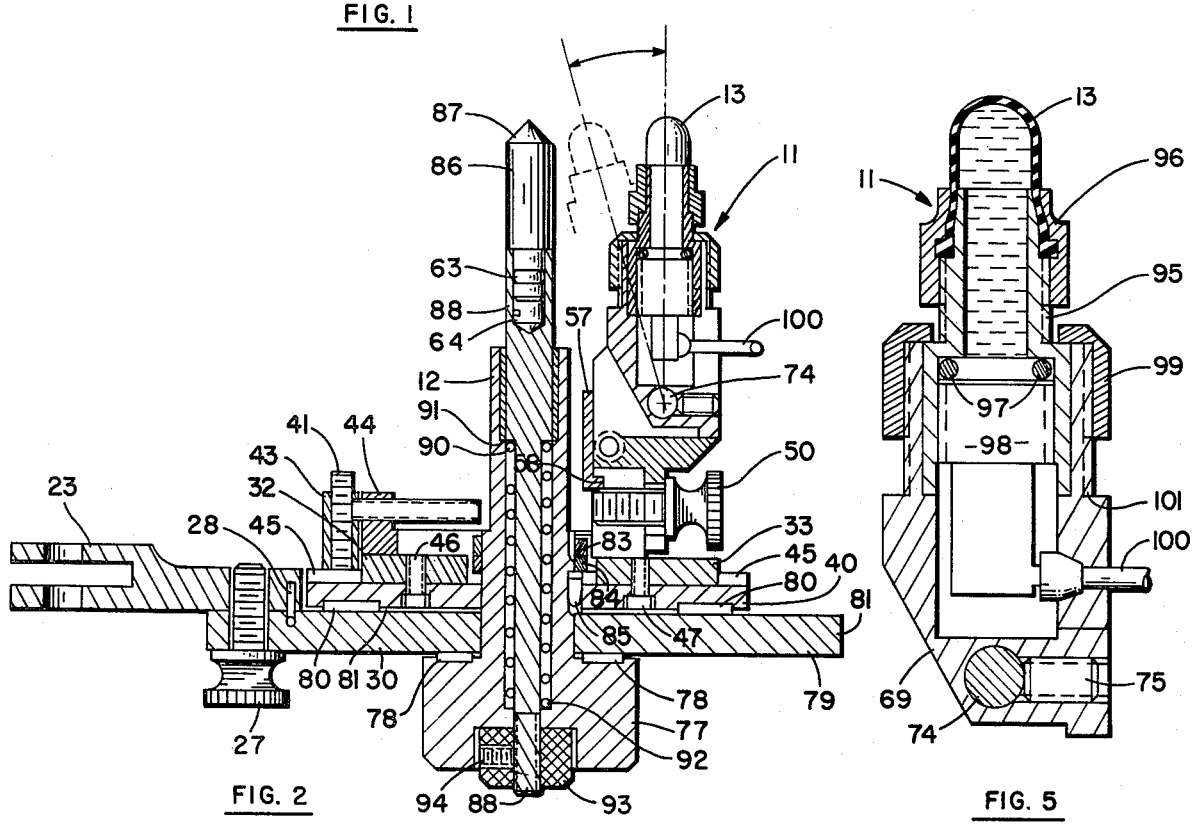
FIG. 2 is a cross-sectional view of the ultrasonic scanner taken along line 2—2 of FIG. 1.
FIG. 5 is an enlarged cross-sectional view showing the detail construction of the transmitting/receiving head assembly illustrated in FIGS. 1 and 2.

Angular adjustment of the leg clevis 23 is accomplished by loosening the leg locking screw 27 until a pin 28, which is press-fitted into the leg clevis 23 as best seen in FIG. 2, is free of a given hole 29 located in the base plate 30. The leg clevis 23 may then be rotated until the pin 28 is in line with the desired hole 29. The leg locking screw 27 may again be tightened with the pin 28 inserted in a desired hole to assure the clevis 23 cannot rotate relative to the base plate 30.

As previously described, the transmitting/receiving head assembly 11 is adjustable along two linear axes. The first linear axis is defined by a line 2—2 taken along a longitudinal axis extending through a first key guide member 32 and a second key guide member 33.

Figure 3:
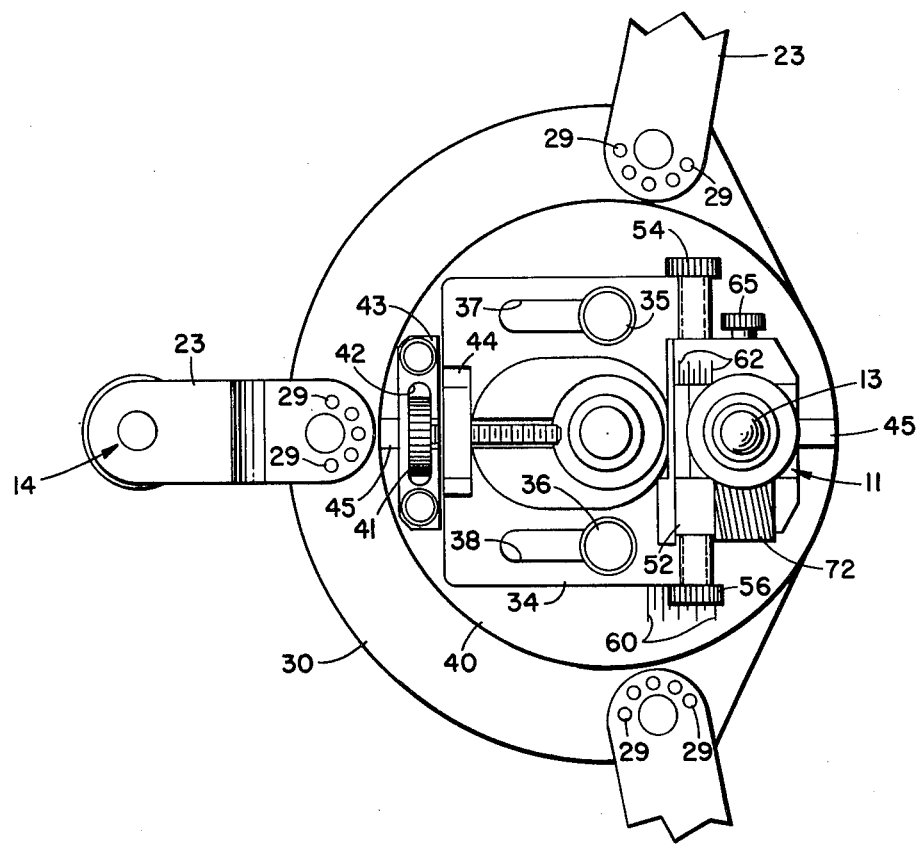
FIG. 3 is a top view illustrating details of the ultrasonic scanners adjustment means.

The method used to adjust the transmitting/receiving head assembly 11 along the first linear axis is to loosen two identical bracket lock screws 35 and 36 (best seen in FIG. 3) which extend through a first locking slot 37 and a second locking slot 38. Both bracket locking screws 35 and 36 are threadably received in a rotatable plate 40. A spindle clearance slot 39 is provided through the center section of an "L" shaped bracket 34. The purpose of the slots 37, 38 and 39 is to permit unobstructed movement of the "L" shaped bracket 34 during first axis linear adjustment.

The mechanism used to move the "L" shaped bracket 34 along the first linear axis includes a first axis adjustment screw 41, the head of which is rotatably mounted in a recess 42 provided in a block member 43 which is mounted on a rotatable plate 40, by any convenient means, and threadably received in an adjustment block 44 which is attached to the "L" shaped bracket 34 by any convenient means.

To adjust the transmitting/receiving head assembly 11 along the first linear axis, the first axis adjustment screw 41 is rotated causing the "L" shaped bracket 34 to move linearly, guided by the key members 32 and 33.

The key members 32 and 33 are held in a keyway 45 provided in one surface of the rotatable plate 40 by screws 46 and 47 (best seen in FIG. 2). The key members 32 and 33 are free to slide in a mating keyway 48 provided in the "L" shaped bracket 34. After the first axis adjustment is complete, bracket lock screws 35 and 36 may be tightened to prevent accidental movement of the transmitting/receiving head assembly 11 along the first linear axis.

The second linear axis, along which the transmitting/receiving head assembly 11 is adjusted, is defined as an axis perpendicular to an axis running lengthwise of the key members 32 and 33.

The method used to adjust the head assembly along the second linear axis is to first loosen a second axis lock screw 50 which extends through a slot 51 provided in a yoke 52 and threadably received in a first leg portion 53 of the "L" shaped bracket 34. The head assembly 11 may then be adjusted along the second linear axis by rotating double headed screw 54 which is threaded through the full length of the yoke 52 and has its heads 55 and 56, respectively, in friction contact with the leg portion 53 of the "L" shaped bracket 34.

A guide member 57, which includes a tongue portion 58 along one edge thereof, is attached to the yoke 52 by any suitable means. The tongue portion 58 mates with a groove 59 provided in the leg portion 53 of the "L" shaped bracket 34 to assure accurate linear adjustment of the head assembly 11 along the second linear axis.

After the head assembly 11 is adjusted to the desired position along the second linear axis, the second axis lock screw 50 may be tightened to prevent accidental movement of the head assembly 11. The head assembly 11 may be rotated relative to the leg portion 53 of the "L" shaped bracket 34 by first loosening an angular rotational lock screw 65.

Figure 4:
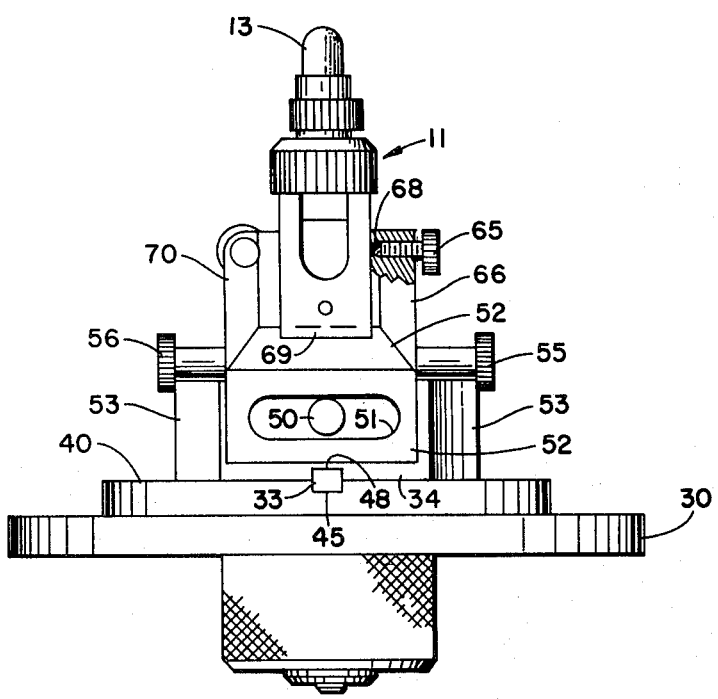
FIG. 4 is an end view of the ultrasonic scanner, further illustrating the scanners adjustment means.

Referring now to FIG. 4, the angular rotational lock screw 65 is threaded through a first upstanding member 66 of a yoke 52 and utilizes a nylon tip 68 to urge the base unit 69 of the head assembly 11 against a second upstanding member 70 of the yoke 52 thereby creating a friction lock between the base unit 69 and the second upstanding member 70. After the angular rotational lock screw 65 is loosened, the angle of the head assembly 11 may be adjusted by rotating a worm gear adjustment knob 71 (best seen in FIG. 1). The worm gear adjustment knob 71 rotates a worm gear 72 which in turn rotates a pinion drive gear 73 mounted on a rotatable shaft 74 which is secured to the base unit 69 by a set screw 75 (best seen in FIG. 5).

As will be noted, the adjustment along the first and second linear axis as well as the angular rotation of the head assembly 11 are all made without the use of tools of any kind and, as can be seen by referring to FIG. 1, vernier scales are conveniently located along each of the adjustable axes. A first vernier scale 60 which indicates relative movement along the first linear axis is located such that a marker portion is inscribed in the "L" shaped bracket 34 and a scale portion is inscribed in the rotatable plate 40. A second vernier scale 61 which indicates relative movement along the second linear axis is located such that a marker portion is inscribed in the guide member 57 and a scale portion inscribed in the leg portion 53 of the "L" shaped bracket 34 and a third vernier scale 62 which shows relative movement between the head assembly 11 and the yoke 52 is located such that a marker portion is inscribed in the head assembly 11 and its associated scale is inscribed in the first upstanding member 66.

Referring to FIG. 2. The head assembly 11 may be rotated 360° about the longitudinal axis of the contact spindle 12 by rotating a spindle knob 77 located on, and forming, a first end of the contact spindle 12. The spindle knob 77 is provided with a first spindle needle bearing 78 which is held in contact with a first surface 79 of the base plate 30. A second needle bearing race 80 is held captive between a second surface 81 of the base plate 30 and the rotatable plate 40.

The spindle 12 slip-fits through both the base plate 30 and the rotatable plate 40 and together with two threaded lock rings 83 and 84, respectively, which are threadably received on the spindle 12, and an expansion pin 85 which is slip-fitted in a groove provided in the spindle 12 and rotatable plate 40 holds the rotatable plate 40 and base 30 in their respective positions and provides the means for the spindle 12 to rotate the head assembly 11.

A replaceable indexing tip 86 is utilized to establish the exact point around which the head assembly 11 is rotated. The indexing tip 86 shown is provided with a pointed end 87 which mates with a punch mark or indentation provided in the fasteneer or structure under evaluation (not shown). It is important to note that the indexing tip 86 need not terminate with a pointed end as shown. Its interchangeability permits other configurations of tips (not shown) to be used such as hex-head, slot, box-end or suction-pad to be interchanged in the matter of a few seconds and assures compatibility with any type of fastener or surface.

The indexing tip 86 is releasably held in a spindle rod 88 that extends through the length of the contact spindle 12. The indexing tip 86 is held in place by friction exerted by a circular spring 63 which is "C" shaped in cross-section and retained in a recess 89 provided in the indexing tip 86. The circular spring 63 exerts sufficient friction in a counter bore 64, provided in one end of the contact spindle 12, to hold the indexing tip 86 in place and yet allows it to freely rotate when provided with other than a pointed end.

The spindle rod 88 is spring-loaded within the contact spindle 12 by means of a compression spring 90 operating between a shoulder 91 provided on the spindle rod 88 and an undercut section 92 provided within the spindle knob 77. A threaded knurled nut 93 is threadably received on the end of the spindle rod 88 which provides means to adjust the height of the indexing tip 86 relative to head assembly 11. A set screw 94 is provided in the knurled nut 93 to prevent accidental height-adjustment of the indexing tip 86 during use of the present invention.

Referring now to FIG. 5. The head assembly 11 comprises the liquid filled boot 13 which is held in leak-proof contact with a sound-coupling portion 95 by a threaded coupling ring 96. The sound-coupling portion 95 houses an "O" ring 97 and a standard ultrasonic combined transmitter/receiver 98 which threads into the sound-coupling portion 95 and in cooperation with the "O" ring 97 seals in a liquid. The liquid may be water or a light oil which has the same, or substantially the same, index of refraction as the ultrasonic beams. The sound-coupling portion 95 is attached to the base unit 69 by a threaded base unit ring 99.

A control wire assembly 100 extends from the ultrasonic combined transmitter/receiver 98 through a cavity 101 provided in the base unit 69 and connects to a standard electronic control and measuring device (not shown).

OPERATION

As previously stated, the primary purpose of the present invention is to determine if a flaw or discontinuity such as a fatigue crack exists around a given point in a structure, such as an aircraft bulkhead (not shown) which is to be inspected for fatigue cracks around a plurality of button-head rivets (not shown) used to hold the bulkhead together.

The preferred method to perform such an inspection is to first connect the transmitter receiver 98 to a standard signal generator and material tester set (not shown), which equipment is commercially available from Magnaflux Corporation, Automation Industries, Sonics, Inc., to name a few. Another commercially available equipment under the brand name Krautkramer-Branson (Model No. KB 6000) is suitable.

Next, an indexing tip is selected which has a concave tip (not shown) which mates with the button-head rivet. The concave indexing tip is then inserted into the contact spindle 12. The head assembly 11 may then be adjusted relative to the structure whereby an ultrasonic beam emitted from the ultrasonic transmitter/receiver 98 passes through the liquid filled boot 13 and impinges on the surface of the structure (not shown) at any point along the periphery of the head of the button-headed rivet.

It is desirable that the outside surface of the liquid filled boot 13 be coated with a light oil prior to use. The light oil coating acts as a wiper and assures an uninterrupted signal path between the liquid filled boot 13 and the structure under inspection.

After the present invention is adjusted, as described above, the transmitting/receiving head 98 and standard recording devices is energized.

The spindle knob 77 may then be rotated causing the liquid filled boot 13 to move around the periphery of the selected rivet, (not shown) while at the same time, an ultrasonic beam is transmitted by, and reflected back, to the ultrasonic combined transmitter/receiver 98 for monitoring and recording. As long as a uniform or maximum reflection of the ultrasonic beam is received, there is no flaw, crack or other discontinuity in the section of the structure under inspection. This is true even though the surface of the structure is plated or painted.

On the other hand, if there is a crack in the structure, then the return or reflected ultrasonic beam will not be uniform and the signal level will be less than maximum as the liquid filled boot 13 moves over the surface area of the flaw. Once a crack is discovered, its perimeters, that is to say its width, length and depth can be accurately measured either by utilizing standard electronic recording devices (not shown) or by the scanner vernier scales 60, 61 and 62 respectively. Its width can be measured by sweeping the liquid filled boot 13 back and forth across the top of the crack. Its length can be measured by incrementally adjusting the liquid filled boot 13 along the first linear axis and sweeping the head assembly 11 back and forth across the crack until the end point of the flaw is established or, alternatively, the length of the crack can be determined by incrementally rotating the head assembly 11 relative to the leg portion 53 and sweeping the head assembly 11 back and forth across the crack. In making this incremental head assembly adjustment, it is not necessary to adjust the height of the head assembly 11 relative to the surface of the structure under evaluation (not shown). The liquid filled boot 13 which is the coupling element between the ultrasonic combined transmitter/receiver 98 and the structure under evaluation is adapted to change configurations without effecting signal return as the head is moved through an arc which varies the distance between the ultrasonic combined transmitter/receiver 98 and the structure under inspection.

It is this feature of the liquid filled boot 13 that makes it possible for the present invention to operate on any surface regardless of its configuration—that is, the surface can be flat, concave, convex, or any combination thereof.

To determine the depth of the crack, the transmitting-/receiving head assembly 11 is adjusted along the second linear axis to a point where an ultrasonic beam emitted by the ultrasonic combined transmitter/receiver 98 is substantially tangential to the shaft of the rivet (not shown) and reflected off the top portion of the structure under inspection. Next, the transmitting-/receiving head assembly 11 is rotated around the contact spindle until the emitted ultrasonic beam is reflected off the top edge of the crack.

The depth of the crack can then be determined by rotating the transmitting/receiving head assembly 11 relative to the depth of the structure and monitoring the signal return. The depth of the crack at various points along the length thereof can be determined by incrementally adjusting the head assembly along the second linear axis and repeating the above procedure.

While the present invention has been described in language more or less specific as to structural features, it is to be understood that the invention is not limited to the specific features and method of operation disclosed and the invention is, therefore, claimed in any of its forms or modifications within the legitimate and valid scope of the appended claims.

We claim:

1. Hand-held ultrasonic scanner apparatus for detecting and measuring flaws in a structure comprising:
    (a) a base plate member including adjustable leg means mounted thereto,
    (b) a spindle means rotatably attaching a rotatable plate member to said base plate member, and
    (c) an ultrasonic transmitter/receiver head assembly adjustably mounted on said rotatable plate member,
    (d) wherein said leg means includes a plurality of legs, one end of each of said legs being provided with a swivel pad to protect the surface of said structure from damage and to compensate for any variation in the contour of said structure, and adjustment means on the other end of said leg cooperating with clevis means for leg length and angular adjustment relative to said base plate.

2. Hand-held ultrasonic scanner apparatus for detecting and measuring flaws in a structure comprising:
    (a) a base plate member including adjustable leg means mounted thereto,
    (b) a spindle means rotatably attaching a rotatable plate member to said base plate member, and
    (c) an ultrasonic transmitter/receiver head assembly adjustably mounted on said rotatable plate member,
    (d) wherein said spindle means includes a spindle rod and a replaceable indexing tip held therein, and wherein said indexing tip is releasably held in said spindle by friction exerted by a circular "C" shaped spring.

3. Hand-held ultrasonic scanner apparatus for detecting and measuring flaws in a structure comprising:
    (a) a base plate member including adjustable leg means mounted thereto,
    (b) a spindle means rotatably attaching a rotatable plate member to said base plate member, and
    (c) an ultrasonic transmitter/receiver head assembly adjustably mounted on said rotatable plate member,
    (d) wherein said spindle means includes a spindle rod and a replaceable indexing tip held therein, said spindle rod being provided with means to adjust the height of said indexing tip relative to said ultrasonic transmitter/receiver head assembly.

4. Hand-held ultrasonic scanner apparatus for detecting and measuring flaws in a structure comprising:
    (a) a base plate member including adjustable leg means mounted thereto,
    (b) a spindle means rotatably attaching a rotatable plate member to said base plate member, and
    (c) an ultrasonic transmitter/receiver head assembly adjustably mounted on said rotatable plate member,
    (d) wherein said ultrasonic transmitter/receiver head assembly is provided with adjustable and locking means along two linear axes and one angular axis relative to said spindle means.

5. The apparatus of claim 4 wherein one or more of said axes are provided with vernier scale means.

6. Hand-held ultrasonic scanner apparatus for detecting and measuring flaws in a structure comprising:
    (a) a base plate member having adjustable legs mounted thereto;
    (b) a rotatable plate member;
    (c) spindle means for rotatably attaching the rotatable plate to the base plate;
    (d) a bracket attached to the rotatable plate by bracket adjustment means permitting the position of the bracket relative to the rotatable plate to be adjusted along two linear axes perpendicular to each other and to the rotational axis of the rotatable plate; and
    (e) an ultrasonic transmitter/receiver head assembly mounted on the bracket.

7. The apparatus of claim 6, wherein the bracket adjusting means comprises a worm gear.

8. The apparatus of claim 6, wherein the ultrasonic transmitter/receiver head assembly transmits and receives ultrasonic waves along a linear transmission axis, and wherein the head assembly comprises means for adjusting the angle between the transmission axis and the axis of rotation of the rotatable plate member.

9. The apparatus of claim 8, wherein the angle adjusting means comprises a worm gear.

* * * * *